United States Patent [19]

Law

[11] Patent Number: 5,106,713
[45] Date of Patent: Apr. 21, 1992

[54] PHOTOCONDUCTIVE IMAGING MEMBERS WITH UNSYMMETRICAL SQUARAINE COMPOSITIONS

[75] Inventor: Kock-Yee Law, Penfield, N.Y.

[73] Assignee: Xerox Corporation, Stamford, Conn.

[21] Appl. No.: 588,395

[22] Filed: Sep. 26, 1990

[51] Int. Cl.[5] .................. C07C 85/00; C07C 85/02
[52] U.S. Cl. ........................................ 430/59; 430/74;
564/307; 564/305; 564/381
[58] Field of Search .................. 430/59, 74; 564/305,
564/307, 381

[56] References Cited

U.S. PATENT DOCUMENTS

| | | | |
|---|---|---|---|
| 4,415,639 | 11/1983 | Horgan | 430/57 |
| 4,607,124 | 8/1986 | Kazmaier et al. | 564/307 |
| 4,624,904 | 11/1986 | Kazmaier et al. | 430/59 |
| 4,746,756 | 5/1988 | Kazmaier et al. | 564/307 |
| 4,886,722 | 12/1989 | Law et al. | 430/59 |

*Primary Examiner*—Marion E. McCamish
*Assistant Examiner*—S. Rosasco
*Attorney, Agent, or Firm*—E. O. Palazzo

[57] ABSTRACT

The cyclized squaraines essentially as represented by the formula wherein $R_1$ and $R_2$ are independently selected from alkyl and hydrogen; $R_3$ and $R_4$ are independently selected from alkyl and benzyl; X is hydrogen, hydroxy, alkyl, alkoxy or halogen; and m is a number of from zero to about 3; and layered imaging members thereof.

48 Claims, 1 Drawing Sheet

PHOTOCONDUCTIVE IMAGING MEMBERS WITH UNSYMMETRICAL SQUARAINE COMPOSITIONS

BACKGROUND OF THE INVENTION

This invention is generally directed to squaraine compositions, and to processes for the preparation thereof. More specifically, the present invention is directed to cyclized unsymmetrical squaraines which can be synthesized by cycloaddition-condensation processes, thereby avoiding the use of costly squaric acid as a reactant. In one ebodiment of the present invention there are provided unsymmetrical squaraine compositions containing alkylenedioxyaryl, including methylenedioxyaryl substituents with improved xerographic properties, inclusive of high charge acceptance, low dark decay, high photosensitivity, and improved cyclic stability when these compositions are incorporated into photoconductive imaging members. The squaraines can be prepared in embodiments of the present invention by cycloaddition-condensation processes thereby avoiding the use of costly squaraic acid as a reactant. Also, in an embodiment of the present invention there are provided cyclized unsymmetrical squaraines, imaging members thereof with the advantages indicated herein in embodiments of the present invention, processes for the preparation thereof, and novel squaraines. In another embodiment of the invention of the present application there are provided imaging members with photoconductive layers comprised of the unsymmetrical squaraines illustrated herein, and charge or hole transport layers, especially those comprised of aryl amines, which members are sensitive to light in the wavelength region of from about 400 to about 1,000 nanometers. The resulting members are responsive to visible light and infrared illumination originating from laser printing apparatuses wherein, for example, gallium arsenide diode lasers are selected. The photoresponsive imaging members of the present invention can also, for example, contain situated between a photogenerating layer and a hole transporting layer, or situated between a photogenerating layer and a supporting substrate with a charge transport layer in contact with the photogenerating layer, a photoconductive composition comprised of the unsymmetrical squaraines illustrated herein.

Numerous different xerographic photoconductive members, including members with photogenerating pigments of squaraines and processes thereof, are known. There are also known photoreceptor materials comprised of inorganic or organic materials wherein the charge carrier generating, and the charge carrier transport functions are accomplished by discrete contiguous layers. Additionally, layered photoreceptor materials are disclosed in the prior art, which include an overcoating layer of an electrically insulating polymeric material. Further, there are disclosed in the prior art layered photoresponsive devices including those comprised of separate generating layers, and transport layers as described in U.S. Pat. No. 4,265,990, the disclosure of which is totally incorporated herein by reference; and overcoated photoresponsive materials containing a hole injecting layer, overcoated with a hole transport layer, followed by an overcoating of a photogenerating layer; and a top coating of an insulating organic resin, reference U.S. Pat. No. 4,251,612. Examples of photogenerating layers disclosed in these patents include trigonal selenium and phthalocyanines, while examples of transport layers include certain diamines as mentioned therein. Also, there is illustrated in U.S. Pat. No. 4,415,639, the disclosure of which is totally incorporated herein by reference, the use of squaraine compositions. such as hydroxy squaraines, as a photoconductive layer in an infrared sensitive photoresponsive device. More specifically, there is described in this patent an improved photoresponsive device containing a substrate, a hole blocking layer, an optional adhesive interfacial layer, an inorganic photogenerating layer, a photoconductive composition capable of enhancing or reducing the intrinsic properties of the photogenerating layer, which photoconductive composition is selected from various squaraine compositions, including hydroxy squaraine compositions, and a hole transport layer. Other patents disclosing photoconductive devices with squaraines are U.S. Pat. Nos. 4,471,041; 4,486,520; 4,508,803; 4,507,480; 4,552,822; 4,390,610; 4,353,971; 4,391,888; 4,607,124 and 4,746,756. In the '124 patent, the disclosure of which is totally incorporated herein by reference, there are illustrated processes for the preparation of a squaraine mixture, one of which may be a fluorinated component, see column 5, wherein the known squaric acid reaction is accomplished in the presence of a fluoroaniline, and the use thereof in photoconductive imaging members. The '756 patent, the disclosure of which is totally incorporated herein by reference, illustrates layered imaging members with certain fluorinated squaraines, wherein $R_2$ and $R_3$ may be a heterocyclic, such as 2-pyrolyl, see columns 3, 4, 5 and 6, for example.

Furthermore, there are illustrated in U.S. Pat. No. 4,624,904, the disclosure of which is totally incorporated herein by reference, photoconductive imaging members with unsymmetrical hydroxy squaraine compositions, and aryl amine hole transport layers. The aforementioned unsymmetrical squaraine compounds can be prepared, for example, by the initial preparation of an aryl cyclobutenedione intermediate, followed by the reaction thereof with a substituted aniline. More specifically, with respect to method A illustrated in the '904 patent, the aryl cyclobutenedione is prepared by heating with reflux at a temperature of from about 40° to about 50° C., depending on the solvent selected; about 20 millimoles to about 50 millimoles of substituted aniline; from about 60 millimoles to about 150 millimoles of dihalocyclobutenedione; and from about 100 milliliters to about 1,000 milliliters of a Friedel-Crafts solvent inclusive of, for example, carbon disulfide nitrobenzene or methylene chloride. This reaction is accomplished in the presence of from about 200 to about 900 millimoles of a catalyst, such as aluminum chloride, and the resulting substituted aniline is reacted with a hydroxy substituted aniline in the presence of an aliphatic alcoholic solvent. Subsequent to separation, there are obtained the desired unsymmetrical squaraine compounds of the formula as detailed on page 8, beginning at line 10, for example. Also, in U.S. Pat. No. 4,521,621, there are described photoresponsive imaging members containing unsymmetrical squaraines, reference for example the formula in column 7, line 60, by forming a mixture of squaric acid, a primary alcohol, a first tertiary amine, and a second tertiary amine.

In U.S. Pat. No. 4,524,220, the disclosure of which is totally incorporated herein by reference, there is illustrated a squaraine process by the reaction of squaric acid and an aromatic aniline in the presence of an aliphatic amine. Also, in U.S. Pat. No. 4,524,219 there is described a process for the preparation of squaraines by the reaction of an alkyl squarate and an aniline in the presence of an aliphatic alcohol, and an optional acid catalyst. Moreover, disclosed in U.S. Pat. No. 4,524,218 are processes for the preparation of squaraines by the reaction of squaric acid with an aromatic amine, and a composition selected from the group consisting of phenols, and phenol squaraines, which reaction is accomplished in the presence of an aliphatic alcohol, and an optional azeotropic catalyst. Other processes for preparing squaraines are illustrated in U.S. Pat. No. 4,525,592, wherein there is described the reaction of a dialkyl squarate, and an aniline in the presence of an aliphatic alcohol and an acid catalyst; and U.S. Pat. No. 4,746,756 mentioned herein wherein the fluorinated squaraines disclosed are prepared by the reaction of an aromatic fluorinated amine and squaric acid in the presence of an aliphatic alcohol and an optional azeotropic cosolvent.

In U.S. Pat. No. 4,886,722, the disclosure of which is totally incorporated herein by reference, there is illustrated the provision of certain unsymmetrical squaraine compositions and processes for the preparation thereof. More specifically, there are disclosed in the '722 patent photoconductive imaging members containing as photoconductive compositions unsymmetrical noncyclized squaraines of the following formula wherein $R_1$, $R_2$ and $R_3$ are independently selected from alkyl groups or aryl groups; X is hydroxy, hydrogen, alkyl, alkoxy, or halo; n is a number of from 1 to about 3; and m is a number of from 0 to about 2. Preferred halogens include fluorine and chlorine. Examples of alkyl groups include those containing from about 1 to about 25 carbon atoms such as methyl, ethyl, propyl, butyl, pentyl, hexyl, heptyl, dodecyl and the like; while examples of aryl groups include those with from about 6 to about 24 carbon atoms including substituted aryl groups such as phenyl and benzyl. Alkoxy groups are represented by those containing from about 1 to about 10 carbon atoms such as methoxy, propoxy, butoxy, pentoxy, heptoxy, and the like, inclusive in some situations of aryl alkoxy substituents such as phenyl alkoxy. Halo includes fluoride, bromide, chloride and iodide.

Specific examples of unsymmetrical squaraines illustrated in the '722 patent include 4-dimethylaminophenyl-4'-methoxyphenyl squaraine; 2-hydroxy-4-dimethylaminophenyl-4'-methoxyphenyl squaraine; 2-methyl-4-dimethylaminophenyl-4'-methoxyphenyl squaraine; 2-fluoro-4-dimethylaminophenyl-4'-methoxyphenyl squaraine; 2-methoxy-4-dimethylaminophenyl-4'-methoxyphenyl squaraine; 4-benzylmethylaminophenyl-4'-methoxyphenyl squaraine; 4-dimethylaminophenyl-3',4'-dimethoxyphenyl squaraine; 2-hydroxy-4-dimethylaminophenyl-3',4'-dimethoxyphenyl squaraine; 2-methyl-4-dimethylaminophenyl-3',4'-dimethoxyphenyl squaraine; 2-fluoro-4-dimethylaminophenyl-3',4'-dimethoxyphenyl squaraine; 2-methoxy-4-dimethylaminophenyl-3',4'-dimethoxyphenyl squaraine; 4-dimethylaminophenyl-3',4',5'-trimethoxyphenyl squaraine; 2-hydroxy-4-dimethylaminophenyl-3',4',5'-trimethoxyphenyl squaraine; 2-chloro-4-dimethylaminophenyl-4'-methoxyphenyl squaraine; 2-chloro-4-dimethylaminophenyl-3',4'-dimethoxyphenyl squaraine; 4-diethylaminophenyl-4'-methoxyphenyl squaraine; and 4-diethylaminophenyl-3',4'-dimethoxyphenyl squaraine.

The squaraine compositions of the '722 patent are generally prepared by a cycloaddition-condensation reaction. More specifically, these squaraines can be prepared by condensing, for example, a 1-alkoxyaryl-2-hydroxycyclobutene-3,4-dione derivative with an N,N-dialkylaniline derivative, such as 1-3',4'-dimethoxyphenyl-2-hydroxycyclobutene-3,4-dione or 3-fluoro-N,N-dimethylaniline in a molar ratio of about 1 to 6, and preferably in a ratio of about 1 to 3 in the presence of an aliphatic alcohol, such as propanol, and an optional drying reagent. About 500 milliliters of alcohol per 0.1 mole of 1-alkoxyaryl-2-hydroxycyclobutene-3,4-dione are selected, however, up to about 1,000 milliliters of alcohol to about 0.5 to 1 mole of 1-alkoxyaryl-2-hydroxycyclobutene-3,4-dione can be selected. The drying reagent can be heterogeneous, such as molecular sieves, or homogeneous, such as a trialkyl orthoformate. A ratio of 1 to 10 equivalents of drying reagent, more specifically tributyl orthoformate, can be used with a ratio of about 1 to 4 to the cyclobutene dione being preferred. Also, the reaction is generally accomplished at a temperature of about 60° C. to about 130° C., and preferably at a temperature of 70° C. to about 100° C. with stirring until the reaction is completed. Subsequently, the desired product can be isolated from the reaction mixture by known techniques such as filtration, and the product is identified by analytical tools including IR, NMR, and mass spectrometry. Further, carbon, hydrogen, fluorine, nitrogen and oxygen elemental analysis can be selected for aiding the identification of the product.

The 1-alkoxyaryl-2-hydroxycyclobutene-3,4-dione reactant can be prepared as indicated in the literature, and specifically by a known [2+2] cycloaddition process involving a tetraalkoxy olefin and an alkoxyarylketene generated in situ by the reaction of an alkoxyarylacetyl chloride and a base. Thus, for example, 3,4-dimethoxyphenylacetyl chloride can be reacted with tetraethoxyethylene in n-hexane in the presence of triethylamine. The ratio of acid chloride to tetraethoxyethylene is about 1 to 10 with 1 to 4 being preferred. The amount of triethylamine used will vary, however, usually an amount equivalent to the amount of the acid chloride is selected, and the reaction mixture is stirred at room temperature until the reaction is complete. Also, the [2+2] cyclo adduct product mixture can be hydrolyzed directly by refluxing in an aqueous hydrochloric acid solution or pre-purified by stirring with silica gel or alumina in a solvent, such as n-hexane or ether, before the hydrolysis. The hydrolyzed product is then purified by conventional technique such as recrystallization. This results in reactants such as 1-4'-methoxyphenyl-2-hydroxycyclobutene-3,4-dione, 1-3',4'-dimethoxyphenyl-2-hydroxycyclobutene-3,4-dione, and 1-3',4',5'-trimethoxyphenyl-2-hydroxycyclobutene-3,4-dione, which can then be reacted with a N,N-dialkylaniline enabling the formation of the unsymmetrical squaraines.

The squaraines of the aforementioned '722 patent can be incorporated into various photoconductive imaging members. One such member is comprised of a supporting substrate, a hole transport layer and as a photoconductive layer situated between the supporting substrate, and the hole transport layer the squaraines. In another embodiment of the copending application, there is envisioned a layered photoresponsive device comprised of a supporting substrate, a certain squaraine photoconductive layer and situated between the supporting substrate and the photoconductive layer, a hole transport layer. In one specific illustrative embodiment of the copending application, the photoresponsive device can be comprised of (1) a supporting substrate, (2) a hole blocking layer, (3) an optional adhesive interface layer, (4) an unsymmetrical squaraine photogenerating layer, and (5) a hole transport layer. Thus, a specific photoresponsive device of the copending application can be comprised of a conductive supporting substrate, a hole blocking metal oxide layer in contact therewith, an adhesive layer, an unsymmetrical squaraine photogenerating material overcoated on the optional adhesive layer, and as a top layer, a hole transport layer comprised of certain diamines dispersed in a resinous matrix. The photoconductive layer composition, when in contact with the hole transport layer, is capable of allowing holes generated by the photogenerating layer to be transported. Examples of aryl amine hole transport molecules that may be selected for the photoconductor devices are illustrated in U.S. Pat. No. 4,265,990, the disclosure of which is totally incorporated herein by reference.

The photoresponsive devices described in the '722 patent and the imaging members of the present invention can be utilized in various imaging systems including xerographic imaging processes. Additionally, the imaging members of the present invention can be selected for imaging and printing systems with visible light and/or infrared light. In this embodiment, the photoresponsive devices may be negatively charged, exposed to light in a wavelength of from about 400 to about 850 nanometers, either sequentially or simultaneously, followed by developing the resulting image and transferring to paper. The above sequence may be repeated many times.

The following prior art is also mentioned: U.S. Pat. Nos. 4,521,621; 4,607,124 and 4,746,756, mentioned hereinbefore, of which the '756 patent illustrates fluorinated squaraines wherein $R_1$, $R_2$ and $R_3$ may be a heterocyclic, see column 5, lines 4 to 29, for example. Further, in *Angew Chem. Int. Ed. Engl* 5, 894 (1966), H. E. Spenger and W. Ziegenbein there is illustrated the preparation of squaraines by condensing one equivalent of squaric acid and two equivalents of aniline derivatives under azeotropic conditions; many squaraines have been prepared by the aforementioned processes, reference for example U.S. Pat. Nos. 3,617,270; 3,824,099; 4,175,956; 4,486,520 and 4,508,803; and hydroxy and certain fluorinated squaraines for xerographic photoreceptor applications, reference K. Y. Law and F. C. Bailey, *J. Imaging Science*, 31, 172 (1987).

In copending application U.S. Ser. No. 524,947, the disclosure of which is totally incorporated herein by reference, there are illustrated photoconductive imaging members with photoconductive fluorinated squaraine compositions of the formulas indicated including bis(2-fluoro-4-N-pyrrolidinophenyl) squaraine; 2-fluoro-4-N-pyrrolidinophenyl-4'-dimethylaminophenyl squaraine; 2-fluoro-4-N-pyrrolidinophenyl-2'-hydroxy-4'-dimethylaminophenyl squaraine; 2-fluoro-4-N-pyrrolidinophenyl-2'-methyl-4'-dimethylaminophenyl squaraine; 2-fluoro-4-N-pyrrolidinophenyl-4'-dimethylaminophenyl squaraine; 2-fluoro-4-N-pyrrolidinophenyl-4'-methoxyphenyl squaraine; 2-fluoro-4-N-pyrrolidinophenyl-3',4'-dimethoxyphenyl squaraine; 2-fluoro-4-N-pyrrolidinophenyl-3',4',5'-trimethoxyphenyl squaraine; 2-fluoro-4-N-pyrrolidinophenyl-2'-methoxy-4'-dimethylaminophenyl squaraine; 2-fluoro-4-N-pyrrolidinophenyl-4'-methylbenzylaminophenyl squaraine; 2-fluoro-4-N-pyrrolidinophenyl-2'-chloro-4'-dimethylaminophenyl squaraine; 2-fluoro-4-N-pyrrolidinophenyl-9'-julolidinyl squaraine; 2-fluoro-4-N-pyrrolidinophenyl-8'-hydroxy-9'-julolidinyl squaraine; and 2-fluoro-4-N-pyrrolidinophenyl-8'-fluoro-9'-julolidinyl squaraine.

Although the above squaraines and processes thereof are suitable for their intended purposes, there continues to be a need for other photoconductive squaraines. Additionally, and more specifically there remains a need for simple, economical processes for preparing certain squaraine compositions with stable properties, which when incorporated into photoconductive devices can result in reduced dark decay characteristics, and increased charge acceptance values as compared to many similar squaraine compositions. In addition, there remains a need for photoconductive imaging members with certain stable electrical characteristics, that is for example the aforementioned imaging members are electrically stable for over 50,000 xerographic imaging cycles in embodiments thereof. In addition, imaging members with the squaraines of the present invention in embodiments thereof are sensitive to a broad range of wavelengths, including visible and infrared light, such as of from about 400 to about 850 nanometers, enabling such members to be useful in electrophotographic imaging and printing processes, including processes wherein diode lasers, or LED (light emitted diodes) image bars are selected.

SUMMARY OF THE INVENTION

It is therefore a feature of the present invention to provide certain squaraine compositions and processes for the preparation thereof.

Another feature of the present invention is to provide certain unsymmetrical squaraine compositions and imaging members comprised of these squaraines, which members are sensitive to wavelengths of from about 400 to about 1,000 and preferably from about 400 to about 850 nanometers.

In another feature of the present invention there are provided improved processes for preparing fluorinated squaraine compositions from alkylenedioxyarylhydroxycyclobutenediones, and photoresponsive imaging members thereof which can possess excellent dark decay properties, high charge acceptance values, and electrical stability.

In yet another feature of the present invention there are provided simple, economical processes for preparing unsymmetrical cyclized squaraines, which can be selected for layered photoconductive imaging members containing aryl amine hole transport layers.

A further feature of the present invention resides in improved processes for obtaining unsymmetrical squaraine compositions of excellent sensitivity, and excellent cyclic stability when incorporated into layered imaging members with hole transport molecules.

Further, in another feature of the present invention there are provided photoconductive imaging members with cyclized unsymmetrical squaraines, which members can be simultaneously responsive to infrared light and to visible light.

Additionally, another feature of the present invention resides in the provision of imaging and printing methods with the photoconductive imaging members illustrated herein.

These and other features of the present invention in embodiments thereof can be accomplished by the provision of squaraine compositions, and processes for the preparation thereof. More specifically, the present invention is directed to photoconductive imaging members with photoconductive cyclized unsymmetrical squaraine compositions represented by the following Formula I:

wherein $R_1$ and $R_2$ independently represent aliphatic and aromatic groups, and more specifically wherein $R_1$ and $R_2$ are alkyl or hydrogen; $R_3$ and $R_4$ are aliphatic and aromatic groups such as alkyl or benzyl; X is hydrogen, halogen, such as fluorine, or chlorine, alkyl such as methyl, alkoxy such as methoxy, hydroxy, alkyl such as methyl or ethyl; and m represents the number of X substituents, and is a number, for example, of 0 (zero), 1, 2, or 3.

Examples of alkyl and alkoxy groups include those containing from about 1 to about 25, and preferably 12 carbon atoms such as methyl, ethyl, propyl, butyl, pentyl, pentoxy, hexyl, hexoxy, heptyl, heptoxy, octyl, nonyl, dodecyl and the like; while examples of aryl groups include those with from about 6 to about 24 carbon atoms including substituted aryl groups, such as phenyl, naphthyl and benzyl. Typical alkoxy groups contain from about 1 to about 25, and preferably 12 carbon atoms, such as methoxy, propoxy, butoxy, pentoxy, heptoxy, and the like, inclusive in some situations of aryl alkoxy substituents, such as phenoxy. Halo includes fluoride, bromide, chloride and iodide.

Illustrative examples of specific squaraines of the present invention include 3,4-methylenedioxyphenyl-4'-dimethylaminophenyl squaraine; 3,4-methylenedioxyphenyl-2'-fluoro-4'-dimethylaminophenyl squaraine; 3,4-methylenedioxyphenyl-2'-hydroxy-4'-dimethylaminophenyl squaraine; 3,4-methylenedioxyphenyl-2'-methyl-4'-dimethylaminophenyl squaraine; 3,4-methylenedioxyphenyl-2'-methoxy-4'-dimethylaminophenyl squaraine; 3,4-methylenedioxyphenyl-2'-chloro-4'-dimethylaminophenyl squaraine; 3,4-methylenedioxyphenyl-2',6,'-difluoro-4'-dimethylaminophenyl squaraine; 3,4-methylenedioxyphenyl-4'-N-pyrrolidinophenyl squaraine; 3,4-methylenedioxyphenyl-2'-fluoro-4'-N-pyrrolidinophenyl squaraine; 3,4-methylenedioxyphenyl-8'-fluoro-9'-julolidinyl squaraine; 3,4-methylenedioxyphenyl-2'-hydroxy-4'-N-pyrrolidinophenyl squaraine; 3,4-methylenedioxyphenyl-2'-fluoro-4'-methylbenzyl aminophenyl squaraine; and the like.

The squaraines of the present invention can be prepared from a novel precursor dione wherein, for example, the dialkoxy, especially the dimethoxy groups in the anisyl ring, are rigidized with an alkylene group, such as methylene. In one embodiment, the process comprises initially preparing the corresponding halide, such as the chloride, by the reaction of 3,4-methylenedioxyphenylacetic acid with thionyl halide, such as thionyl chloride, with heating to result in 3,4-methylenedioxyphenylacetyl chloride. The aforementioned chloride can then be reacted with tetraethoxyethylene, followed by hydrolysis of the product after heating enabling the product precursor 1-(3,4'-methylenedioxyphenyl)-2-hydroxycyclobutene-3,4-dione. Subsequently, the resulting aforementioned dione after separation can be reacted with an aniline, such as dimethylaniline, in an alcohol, such as propanol, and an orthoformate, such as tributyl orthoformate, to enable the squaraine 3,4-methylenedioxyphenyl-4'-dimethylaminophenyl squaraine.

In embodiments thereof, the squaraine compositions of the present invention are generally prepared by a cycloaddition-condensation reaction. More specifically, the squaraines can be prepared by condensing, for example, a 1-alkylenedioxyaryl-2-hydroxycyclobutene-3,4-dione derivative with an N,N-dialkylaniline derivative, such as 1-3',4'-methylenedioxyphenyl-2-hydroxycyclobutene-3,4-dione and 3-fluoro-N,N-dimethylaniline in a molar ratio of about 1 to 6, and preferably in a ratio of about 1 to 3 in the presence of an aliphatic alcohol with, for example, from 1 to about 10 carbon atoms, such as propanol, and an optional drying reagent. About 500 milliliters of alcohol per 0.1 moles of 1-alkylenedioxyaryl-2-hydroxycyclobutene-3,4-dione can be selected, however, in embodiments up to about 1,000 milliliters of alcohol to about 0.5 to 1 moles of 1-alkylenedioxyaryl-2-hydroxycyclobutene-3,4-dione can be selected. The drying reagent can be heterogeneous such as molecular sieves, or homogeneous such as a trialkyl orthoformate. A ratio of about 1 to 10 equivalents of drying reagent, such as tributyl orthoformate, can be used with a ratio of about 1 to 4 to the cyclobutene dione being preferred. Also, the reaction can generally be accomplished at a temperature of about 60° C. to about 130° C., and preferably at a temperature of 70° C. to about 100° C. with stirring until the reaction is completed. Subsequently, the desired product can be isolated from the reaction mixture by known techniques such as filtration, and the product can be identified by analytical tools including IR, NMR, and mass spectrometry. Further, carbon, hydrogen, fluorine, nitrogen and oxygen elemental analysis can be selected for aiding the identification of the product.

The 1-alkylenedioxyaryl-2-hydroxycyclobutene-3,4-dione reactant can be prepared as indicated in the literature referred to herein, and specifically by a known [2+2] cycloaddition process involving a tetraalkoxy olefin and an alkylenedioxyarylketene generated in situ by the reaction of an alkylenedioxyarylacetyl chloride and a base. Thus, for example, 3,4-methylenedioxyphenylacetyl chloride can be reacted with tetraethoxyethylene in n-hexane in the presence of triethylamine. The ratio of acid chloride to tetraethoxyethylene is about 1 to 10 with 1 to 4 being preferred. The amount of triethylamine used will vary, however, usually an amount equivalent to the amount of the acid chloride is selected, and the reaction mixture is stirred at room temperature until the reaction is complete. Also, the [2+2] cyclo adduct product mixture can be hydrolyzed directly by refluxing in an aqueous hydrochloric acid solution or prepurified by stirring with silica gel or alumina in a solvent, such as n-hexane or ether, before the hydrolysis. The hydrolyzed product is then purified by conventional technique such as recrystallization. This results in reactants such as 1-(3',4'-methylenedioxyphenyl)-2-hydroxycyclobutene-3,4-dione, which can be reacted with a N,N'-dialkylaniline as indicated herein thus enabling the formation of the unsymmetrical squaraines of the present invention in embodiments thereof.

In an embodiment, the novel precursor dione can be represented by the following formula:

II.

The squaraine compounds of the present invention can be incorporated into various photoconductive imaging members. One such member is comprised of a supporting substrate, a hole transport layer, and as a photoconductive layer situated between the supporting substrate and the hole transport layer the squaraine compositions prepared in accordance with the process of the present invention. In another embodiment, there is envisioned a layered photoresponsive device comprised of a supporting substrate, a photoconductive layer comprised of the squaraine compound of the present invention, and situated between the supporting substrate and the photoconductive layer a hole transport layer. In one specific illustrative embodiment, the photoresponsive device can be comprised of (1) a supporting substrate, (2) a hole blocking layer, (3) an optional adhesive interface layer, (4) an unsymmetrical squaraine photogenerating layer, and (5) a hole transport layer. Thus, a specific photoresponsive device of the present invention can be comprised of a conductive supporting substrate, a hole blocking metal oxide layer in contact therewith, an adhesive layer, an unsymmetrical squaraine photogenerating material overcoated on the optional adhesive layer, and as a top layer, a hole transport layer comprised of certain diamines dispersed in a resinous matrix. The photoconductive layer composition when in contact with the hole transport layer is capable of allowing holes generated by the photogenerating layer to be transported. Examples of aryl amine hole transport molecules that may be selected for the photoconductor devices are illustrated in U.S. Pat. No. 4,265,990, the disclosure of which is totally incorporated herein by reference. Also, examples of charge transport molecules are illustrated in U.S. Pat. No. 4,921,773, and the patents mentioned therein, the disclosures of each of the aforementioned patents, including the '773 patent, being totally incorporated herein by reference.

The photoresponsive devices described herein can be incorporated into various imaging system such as those conventionally known as xerographic imaging processes. Additionally, the imaging members of the present invention can be selected for imaging and printing systems with visible light and/or infrared light. In this embodiment, the photoresponsive devices may be negatively charged, exposed to light in a wavelength of from about 400 to about 850 nanometers, either sequentially or simultaneously, followed by developing the resulting image and transferring to paper. The above sequence may be repeated many times.

BRIEF DESCRIPTION OF THE DRAWINGS

For a better understanding of the features of the present invention, the following detailed description of various preferred embodiments is provided wherein.

DESCRIPTION OF SPECIFIC EMBODIMENTS

Specific embodiments of the invention will now be illustrated, it being noted that substantially equivalent imaging members are also embraced within the scope of the present invention.

Figure 1:
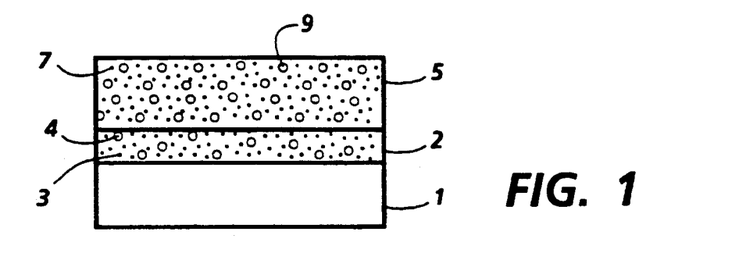
FIGS. 1, 2, and 3 are partially schematic views of examples of photoconductive imaging members of the present invention.

FIG. 1 illustrates a photoconductive imaging member of the present invention comprising a supporting substrate 1, a photogenerating layer 2 comprising the squaraines 3 illustrated herein optionally dispersed in a resinous binder composition 4, and a charge carrier hole transport layer 5, which comprises hole transporting molecules 7 dispersed in an inactive resinous binder composition 9.

Figure 2:
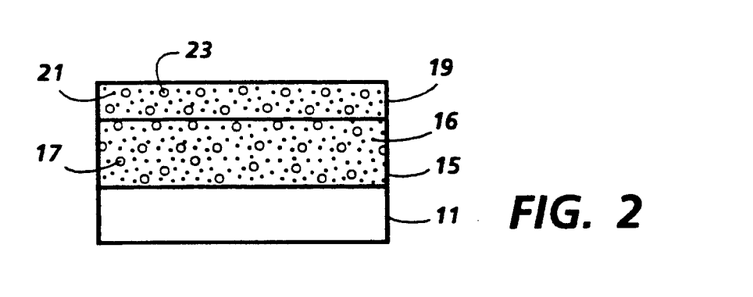

FIG. 2 illustrates the same member as that shown in FIG. 2 with the exception that the hole transport layer is situated between the supporting substrate and the photogenerating layer. More specifically, this Figure illustrates a photoconductive imaging member comprising a supporting substrate 11, a hole transport layer 15 comprising aryl amine hole transport molecules 16 dispersed in an inactive resinous binder composition 17, and a photogenerating layer 19 comprising a squaraine 21 of the formula as illustrated herein, especially 3,4-methylenedioxyphenyl-2'-fluoro-4'-dimethylaminophenyl squaraine optionally dispersed in a resinous binder composition 23.

Figure 3:
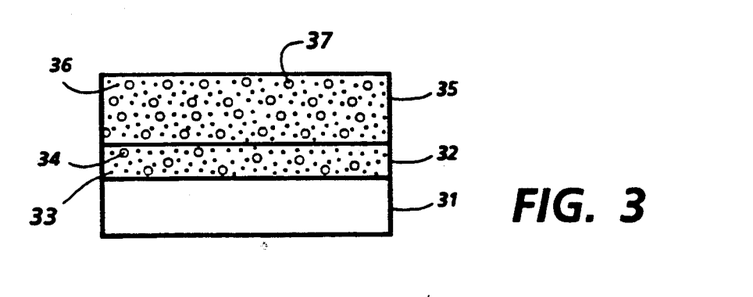

FIG. 3 illustrates a photoconductive imaging member of the present invention comprising a supporting substrate 31, a photogenerating layer 32 comprising the squaraine 33, 3,4-methylenedioxyphenyl-4'-dimethylaminophenyl squaraine, or 3,4-methylenedioxyphenyl-2'-fluoro-4'-dimethylaminophenyl squaraine optionally dispersed in a resinous binder composition 34, and a charge carrier hole transport layer 35, which comprises hole transporting molecules 36, dispersed in an inactive resinous binder composition 37.

The supporting substrate of the imaging members may comprise an insulating material such as an inorganic or organic polymeric material, including Mylar ®, a commercially available polymer; a layer of an organic or inorganic material having a semiconductive surface layer such as indium tin oxide or aluminum arranged thereon; or a conductive material such as aluminum, titanium, chromium, nickel, brass, or the like. The substrate may be flexible, seamless, or rigid and may have a number of different configurations, such as a plate, a cylindrical drum, a scroll, an endless flexible belt, and the like. Preferably, the substrate is in the form of an endless flexible belt. In some situations, it may be desirable to coat an anticurl layer, such as polycarbonate materials commercially available as Makrolon ®, on the back of the substrate, particularly when the substrate is an organic polymeric material.

The thickness of the substrate layer depends on a number of factors, including economic considerations, the components of the other layers, and the like. Thus, this layer may be of substantial thickness, for example over 100 mils, or of minimal thickness provided that there are no adverse effects on the system. In a preferred embodiment, the thickness of this layer is from about 3 mils to about 15 mils.

Generally, the squaraine photogenerating layer has a thickness of from about 0.05 micron to about 10 microns or more, and preferably has a thickness of from about 0.1 micron to about 4 microns. The thickness of this layer, however, is dependent primarily upon the photogenerating weight loading, which may vary from about 5 to 100 percent, the components of the other layers, and the like. Generally, it is desirable to provide this layer in a thickness sufficient to absorb a substantial amount, for example about 90 percent or more, of the incident radiation which is directed upon it in the imagewise or printing exposure step. The maximum thickness of this layer is dependent primarily upon factors such as mechanical considerations, such as the specific squaraine compound selected, the thicknesses of the other layers, and whether a flexible photoconductive imaging member is desired. Optionally, resin binders for the photogeneration layer include poly(vinyl acetal) such as polyvinyl formal, and the like.

The hole transport layer can be comprised of various components providing, for example, that they effectively transport charges (holes) such as an aryl amine compound dispersed in a resinous binder and other components, reference the '773 patent mentioned herein, the disclosure of which is totally incorporated herein by reference. In one embodiment the hole transport layers are comprised of aryl amine compounds of the formula:

wherein X is selected from the group consisting of alkyl and halogen. Preferably, X is selected from the group consisting of methyl and chloride in either the ortho, meta, or para positions. Suitable inactive binder materials for the hole transport layer include known highly insulating resins, which generally have a resistivity of at least $10^{12}$ ohm-cm to prevent undue dark decay. Compounds corresponding to the above formula include N,N'-diphenyl-N,N'-bis(alkylphenyl)-[1,1'-biphenyl]-4,4'-diamine, wherein alkyl is selected from the group consisting of methyl, such as 2-methyl, 3-methyl and 4-methyl, ethyl, propyl, butyl, hexyl, and the like. With halo substitution, the amine is N,N'-diphenyl-N,N'-bis(-halo phenyl)-[1,1'-biphenyl]-4,4'-diamine, wherein halo is 2-chloro, 3-chloro or 4-chloro. Other electrically active small molecules that can be dispersed in the electrically inactive resin to form a layer which will transport holes include bis(4-diethylamino-2-methylphenyl)-phenyl methane, 4',4'''-bis(diethylamino)-2',2'''-dimethyltriphenyl methane, bis-4-(diethylaminophenyl)phenyl methane, and 4,4'-bis(diethylamino)-2,2'-dimethyltriphenyl methane. Generally, the hole transport layer has a thickness of from about 5 to about 75 microns, and preferably of from about 10 to about 40 microns.

Examples of highly insulating and transparent resinous components or inactive binder resinous material for the transport layer include materials such as those described in U.S. Pat. No. 3,121,006, the disclosure of which is totally incorporated herein by reference. Specific examples of suitable organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight of from about 20,000 to about 100,000 with a molecular weight in the range of from about 50,000 to about 100,000 being particularly preferred. The materials most preferred as electrically inactive resinous materials are poly(4,4'-dipropylidine-diphenyline carbonate) with a weight average molecular weight of from about 35,000 to about 40,000 available as Lexan 145 from General Electric Company; poly(4,4'-isopropylidine-diphenyline carbonate) with a weight average molecular weight of from about 40,000 to about 45,000 available as Lexan 141 from General Electric Company; a polycarbonate resin having a weight average molecular weight of from about 50,000 to about 100,000 available as Makrolon from Farbenfabricken Bayer AG; and a polycarbonate having a weight average molecular weight of from about 20,000 to about 50,000 available as Merlon from Mobay Chemical Company. Generally, the resinous binder contains from about 10 to about 75 percent by weight of the active material corresponding to the foregoing formula, and preferably from about 35 percent to about 50 percent of this material. Examples of binder material for the squaraine photogenerating layer are poly(vinyl acetals), polycarbonates as mentioned herein, polyesters, polyvinyl carbazole, and the like. Typical effective amounts of binder can be selected including, for example, from about 5 to about 95, and preferably from about 10 to about 70 weight percent, in embodiments of the present invention, and providing that squaraine enables photogeneration.

The photoconductive imaging member may optionally contain a hole blocking layer situated between the supporting substrate and the photogenerating layer. This layer may comprise metal oxides, such as aluminum oxide and the like, or materials such as silanes. The primary purpose of this layer is to prevent hole injection from the substrate during and after charging. Typically, this layer is of a thickness of less than 50 Angstroms, although it may be as thick as 500 Angstroms in some instances.

In addition, the photoconductive imaging member may also optionally contain an adhesive interface layer situated between the hole blocking layer and the photogenerating layer. This layer may comprise a polymeric material such as polyester, polyvinyl butyral, polyvinyl pyrrolidone and the like. Typically, this layer is of a thickness of less than about 0.6 micron.

Imaging members of the present invention exhibit excellent xerographic properties in embodiments thereof. For example, values for dark development potential ($V_{ddp}$) can range from about −400 to about −975. Preferred ranges for dark development potential for the imaging members of the present invention are usually about −400 to −900 volts with −800 volts being especially preferred in embodiments. High dark development potentials permit high contrast potentials, which result in images of high quality with essentially no background development.

The imaging members of the present invention in embodiments thereof also exhibit low dark decay values of, for example, about −50 volts per second or less. Low dark decay values can be of importance for developing high quality images since dark decay measures the amount of charge that disappears after charging of the photoreceptor, and a large difference in charge between exposed and unexposed areas of the photoreceptor results in images with high contrast. Acceptable values for dark decay vary depending on the design of the imaging apparatus in which the imaging members are contained. This dark decay may be as high as −100 volts per second with −50 volts, and −10 to −20 volts per second being preferred in embodiments.

Residual potential values ($V_R$) for the imaging members of the present invention in embodiments thereof are excellent, ranging from, for example, about −5 volts to about −50 volts. Residual potential is a measure of the amount of charge remaining on the imaging member after erasure by exposure to light and prior to imaging. Residual potentials of −5 to −15 are considered very exceptional.

Photosensitivity values ($E_{0.5ddp}$ at 600 nanometers) for the imaging members of the present invention in embodiments thereof are acceptable and, in some instances excellent, and can be, for example, from about 4 to about 25 ergs per square centimeter. Acceptable photosensitivity values vary depending on the design of the imaging apparatus in which the imaging members are contained; thus in some instances, values as high as 40 or 50 are acceptable, and values of about 5 can be preferred.

The present invention also encompasses a method of generating images with the photoconductive imaging members disclosed herein. The method comprises the steps of generating an electrostatic image on a photoconductive imaging member of the present invention, subsequently developing the electrostatic image with known developer compositions comprised of resin particles, pigment particles, additives, including charge control agents and carrier particles, reference U.S. Pat. Nos. 4,558,108; 4,560,535; 3,590,000; 4,264,672; 3,900,588; and 3,849,182, the disclosures of each of these patents being totally incorporated herein by reference, transferring the developed electrostatic image to a suitable substrate, and permanently affixing the transferred image to the substrate. Development of the image may be achieved by a number of methods, such as cascade, touchdown, powder cloud, magnetic brush, and the like. Transfer of the developed image to a substrate may be by any method, including those wherein a corotron or a biased roll is selected. The fixing step may be performed by means of any suitable method, such as flash fusing, heat fusing, pressure fusing, vapor fusing, and the like.

The imaging members of the present invention can be prepared by a number of different known processes such as those illustrated in the U.S. Pat. No. 4,886,722, the disclosure of which is totally incorporated herein by reference. In one process embodiment, the squaraine photogenerator is coated onto a supporting substrate with a Bird applicator, for example, followed by the solution coating of the charge transport layer, and thereafter drying in, for example, an oven.

The following examples are being supplied to further define various species of the present invention, it being noted that these examples are intended to illustrate and not limit the scope of the present invention. Parts and percentages are by weight unless otherwise indicated.

EXAMPLE I 3,4-methylenedioxyphenyl acetic acid, 50.4 grams, 0.28 mole, was reacted with an excess amount of thionyl chloride, 58 grams, 0.49 moles, in a 250 milliliter round bottom flask at 60° C. for 3 hours. The product mixture resulting was cooled to room temperature, about 25° C., and any excess thionyl chloride was removed with a water aspirator. Pure, about 99.5 percent purity, 3,4-methylenedioxyphenylacetylchloride was isolated as a light reddish oil by vacuum distillation yielding 48.2 grams, an 80 percent yield of product. The boiling point of the aforementioned product was 116° C. at 1.4 millimeters of mercury. IR (neat): 1,795 cm$^{-1}$ (C=O).

EXAMPLE II 1-(3',4'methylenedioxphenyl)-2-hydroxycyclobutene-3,4-dione was synthesized by a (2+2 cycloaddition reaction similar to that reported by Bellus *J. Am. Chem. Soc.*, 100, 8026 (1978), the disclosure of which is totally incorporated herein by reference.

Tetraethoxyethylene, which was freshly synthesized using the procedure of Bellus et al. *Helv. Chim. Acta.*, 63, 1130 (1980), the disclosure of which is totally incorporated herein by reference, (21.8 grams, 0.107 mole), triethylamine (23.6 grams), and n-hexane (450 milliliters) were discharged in a 1 liter three-neck flask which was equipped with a mechanical stirrer and a nitrogen inlet. There was then added dropwise to the n-hexane solution over a two hour period 3,4-methylenedioxyphenylacetyl chloride, 48.2 grams, 0.244 mole. A light yellow precipitate was formed during the addition of the acid chloride. After the addition was completed, the resulting mixture was stirred at room temperature, about 25° C. for 4 hours. Subsequently, the mixture was warmed by a water bath at 60° C. for 1 hour, followed by filtration. The yellow cake obtained was washed with warm, about 40° C., n-hexane (3×1,300 milliliters), and the n-hexane solutions were combined. After removing the solvent under reduced pressure, 30 grams of a yellow residue were obtained. This residue was then hydrolyzed with 120 milliliters, 18 percent, of hydrochloric for 4 hours. The crude product was then isolated by filtration. After recrystallization from a mixture of toluene and acetone, a 1:1 ratio, a light yellow solid which was subsequently identified as 1-(3',4'methylenedioxyphenyl)-2-hydroxycyclobutene-3,4-dione was obtained in a yield of 10.7 grams, 46 percent. The melting point of the aforementioned product was about 225° C. IR (KBr): 1,722 and 1,795 cm$^{-1}$ (C=O); $^1$H NMR (DMSO-d$_6$): δ6.07 (s, 2H, CH$_2$), 7.04 (d, J=7.9 Hz, 1H), 7.47 (d, J=1.4 Hz, 1H) and 7.59 (AB$_q$, J$_A$=7.9 Hz, J$_B$=1.4 Hz, 1H). Analysis calculated for the above product C$_{11}$H$_6$O$_5$: C-60.56, H-2.77; Found: C-61.46, H-2.73.

EXAMPLE III

The 1-(3',4'methylenedioxyphenyl)-2-hydroxycyclobutene-3,4-dione obtained from Example II, 0.55 grams, 2.5 millimoles, N,N-dimethylaniline, 0.31 grams, 2.5 millimole, tributyl orthoformate, 2 milliliters, and 20 milliliters of 2-propanol were placed in a 100 milliliter 3-neck flask, which was equipped with a magnetic stirrer and a nitrogen inlet. The resulting mixture was stirred and heated to reflux for 2 hours. After cooling to about 0° to 5° C., the precipitated product was isolated by filtration, and the solid product was purified by washing with 2-proponal until the filtrate was light blue in color, followed by rinsing with a small quantity of ether, about 5 milliliters. Thereafter, the mixture was vacuum dried yielding 0.51 gram, 63 percent yield, of a dark blue powder, which was subsequently identified by elemental analysis, and IR as 3,4-methylenedioxyphenyl-4'-dimethylaminophenyl squaraine with a melting point of 219° to 221° C.; IR (KBr): 1,596 cm$^{-1}$ (squaraine). Analysis calculated for the above product $C_{19}H_{15}NO_4$: C-71.02, H-4.71, N-4.36; Found: C-70.32, H-4.73, N-4.02.

EXAMPLE IV

The procedure of Example III was repeated with the exception that 3-fluoro-N,N-dimethylaniline was selected in place of N,N-dimethylaniline yielding 3,4-methylenedioxyphenyl-2'-fluoro-4'-dimethylaminophenylsquaraine, a dark blue solid, 0.24 gram, 28 percent yield; melting point 212° to 216° C. IR(KBr): 1,608 and 1,620 cm$^{-1}$ (squaraine). Analysis calculated for the above product $C_{19}H_{14}NO_4F$: C-67.25, H-4.16, N-4.13, F-5.60; Found: C-66.83, H-4.32, N-3.83, F-5.21.

EXAMPLE V

The procedure of Example III was repeated with the exception that 3-hydroxy-N,N-dimethylaniline was selected in place of N,N-dimethylaniline yielding 3,4-methylenedioxyphenyl-2'-hydroxy-4'-dimethylaminophenyl squaraine, a dark purple blue solid, 0.62 gram, 74 percent yield; melting point 248° to 249° C. IR (KBr): 1,610 and 1,630 cm$^{-1}$ (squaraine). Analysis calculated for the above product $C_{19}H_{15}NO_5$: C-67.65, H-4.48, N-4.15; Found: C-67.49, H-4.50, N-4.07.

EXAMPLE VI

There was prepared a photoresponsive device containing as the photoconductive material the squaraine as prepared in accordance with Example IV, and as a hole transport layer an aryl amine dispersed in a resinous binder. Specifically, there was prepared a photoresponsive device by providing a ball grained aluminum substrate of a thickness of 150 microns, followed by applying thereto with a multiple clearance film applicator, in a wet thickness of 0.5 mil, a layer of N-methyl-3-aminopropyltrimethoxysilane, available from PCR Research Chemicals, Florida, in ethanol in a 1:20 volume ratio. This layer was then allowed to dry for 5 minutes at room temperature, followed by curing for 10 minutes at 110° C. in a forced air oven.

A photoconductive layer containing 80 percent by weight of 3,4-methylenedioxyphenyl-2'-fluoro-4'-dimethylaminophenyl squaraine, and 20 percent by weight of poly(vinyl formal) was then prepared as follows:

In a 2 ounce amber bottle, there was added 0.21 gram of the above squaraine, 0.05 gram of poly(vinyl formal) obtained from Scientific Polymer Products, Inc., formal content 82 percent, acetate content 12 percent, hydroxy content 6 percent, 85 grams of ⅛ inch stainless steel shots and 10 milliliters of methylene chloride. The above mixture was placed on a ball mill for 24 hours. The resulting slurry was then coated on the silane layer using a 0.5 mil wet gap Bird film applicator. The layer was then air dried for 5 minutes, and at 135° C. for 10 minutes in a forced air oven. The dry thickness of the squaraine layer was about 0.4 micron.

The above photoconductive layer was then overcoated with a charge transport layer, which was prepared as follows:

A transport layer composed of 50 percent by weight of Makrolon ®, a polycarbonate resin available from Larbensabricken Bayer A.G., was mixed with 50 percent by weight of the aryl armine N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to provide a layer with a dry thickness of 30 microns over the above squaraine photoconductive layer using a multiple clearance film applicator (5 mils wet gap thickness). The resulting device was then air dried at room temperature for 20 minutes, followed by drying in a forced air oven at 135° C. for 6 minutes.

The above photoreceptor device was then incorporated into a xerographic imaging test fixture and there resulted, subsequent to development of the formed latent images with a toner comprised of 88 percent by weight of styrene n-butyl methacrylate (58/42) resin particles, 10 percent by weight of carbon black, and 3 percent by weight of the charge additive distearyl dimethyl ammonium methyl sulfate, copies of excellent resolution and high quality.

EXAMPLE VII

A photoconductive imaging member was prepared by providing a titanized Mylar substrate in a thickness of 3 mils and applying thereto a layer of silane as described in Example VI, and then a layer of 0.5 percent by weight of E. I. DuPont 49,000 adhesive in methylene chloride and 1,1,2-trichloroethane (4:1 volume ratio) with a Bird Applicator to a wet thickness of 0.5 mil. The layer was allowed to dry for one minute at room temperature, and 10 minutes at 100° C. in a forced air oven. The resulting layer had a dry thickness of 0.5 micron.

In a 2 ounce amber bottle, there was added 0.21 gram of the squaraine, 0.05 gram of poly(vinyl formal), 85 grams of ⅛ inch stainless steel shots and 10 milliliters of methylene chloride. The above mixture was placed on a ball mill for 24 hours. The resulting slurry was then coated on the titanized Mylar substrate, and more specifically onto the 49,000 adhesive layer using a 0.5 mil wet gap Bird Film Applicator. The layer was then air dried for 5 minutes and at 135° C. for 10 minutes in a forced air oven. The dry thickness of the squaraine layer was about 0.4 micron.

The above photoconductive layer was then overcoated with a hole transport layer, which was prepared as follows:

A hole transport layer composed of 50 percent by weight of Makrolon ®, a polycarbonate resin available from Larbensabricken Bayer A.G., was mixed with 50 percent by weight N,N'-bis(3-methylphenyl)-1,1'-biphenyl-4,4'-diamine. This solution was mixed to 9 percent by weight in methylene chloride. All of these components were placed in an amber bottle and dissolved. The mixture was coated on the above squaraine photogenerating layer to provide a layer with a dry thickness of 30 microns, which coating was accomplished with a multiple clearance film applicator, 5 mils wet gap thickness. The resulting device was then air dried at room temperature for 20 minutes, followed by drying in a forced air oven at 135° C. for 6 minutes.

The above photoreceptor device was then incorporated into a xerographic imaging test fixture wherein latent images were generated on the photoreceptor. There resulted, subsequent to development of the images with toner particles containing a styrene n-butylmethacrylate resin, 88 percent, 10 percent of carbon black, and 2 weight percent of cetyl pyridinium chloride, and fixing by heat, images of excellent resolution and high quality with substantially no background deposits.

Photoresponsive devices can be prepared by repeating the procedure of Examples VI and VII with the exceptions that there can be selected as the squaraine photoconductive component the other squaraines of the present invention illustrated herein.

The above members can then be tested for photosensitivity in the visible and the infrared region of the spectrum by negatively charging the devices with a corona to $-800$ volts, followed by simultaneously exposing each member to monochromic light from a tungsten lamp in the wavelength region of about 400 to about 900 nanometers. The photoresponsive devices will have excellent response, that is the devices discharged from $-800$ volts to about $-100$ volts at 20 ergs/cm$^2$ in the wavelength region of from about 400 to about 900 nanometers indicating both visible and infrared photosensitivity for these members.

Other modifications of the present invention will occur to those skilled in the art subsequent to a review of the present application. These modifications, and equivalents thereof are intended to be included within the scope of this invention.

What is claimed is:

1. The cyclized squaraines essentially as represented by the formula wherein $R_1$ and $R_2$ are independently selected from alkyl and hydrogen; $R_3$ and $R_4$ are independently selected from alkyl and benzyl; X is hydrogen, hydroxy, alkyl, alkoxy or halogen; and m is a number of from zero to about 3.

2. A squaraine in accordance with claim 1 wherein $R_1$ and $R_2$ are alkyl groups of from 1 to about 6 carbon atoms.

3. A photoconductive imaging member comprised of a supporting substrate, a photogenerating layer comprised of a squaraine of claim 1, and a hole transport layer.

4. A photoconductive imaging member in accordance with claim 3 wherein the photogenerating layer is situated between the supporting substrate and the hole transport layer.

5. A photoconductive imaging member in accordance with claim 3 wherein the hole transport layer is situated between the supporting substrate and the photogenerating layer.

6. A photoconductive imaging member in accordance with claim 3 wherein the photoconductive imaging member includes a metal oxide hole blocking layer situated between the supporting substrate and the photogenerating layer.

7. A photoconductive imaging member in accordance with claim 6 wherein the metal oxide is aluminum oxide.

8. A photoconductive imaging member in accordance with claim 6 wherein the metal oxide hole blocking layer has a thickness of less than about 500 Angstroms.

9. A photoconductive imaging member in accordance with claim 3 wherein the photoconductive imaging member contains an adhesive interface layer situated between the supporting substrate and the metal oxide hole blocking layer.

10. A photoconductive imaging member in accordance with claim 9 wherein the adhesive interface layer comprises a polymeric material selected from the group consisting of polyester, polyvinylbutral, and polyvinyl pyrrolidone.

11. A photoconductive imaging member in accordance with claim 9 wherein the adhesive interface layer has a thickness of less than about 0.6 micron.

12. A photoconductive imaging member in accordance with claim 3 wherein the supporting substrate is a metal.

13. A photoconductive imaging member in accordance with claim 12 wherein the metal is aluminum or titanium.

14. A photoconductive imaging member in accordance with claim 3 wherein the supporting substrate is an organic polymeric composition.

15. A photoconductive imaging member in accordance with claim 3 wherein the supporting substrate has a thickness of from about 3 to about 100 mils.

16. A photoconductive imaging member in accordance with claim 3 wherein the supporting substrate has a thickness of from about 3 to about 10 mils.

17. A photoconductive imaging member in accordance with claim 3 wherein the squaraine layer has a thickness of from about 0.05 to about 10 microns.

18. A photoconductive imaging member in accordance with claim 3 wherein the squaraine layer has a thickness of from about 0.1 to about 3 microns.

19. A photoconductive imaging member in accordance with claim 3 wherein the hole transport layer has a thickness of from about 5 to about 50 microns.

20. A photoconductive imaging member in accordance with claim 3 wherein the squaraine compound is dispersed in a resinous binder in an amount of from about 5 percent by weight to about 95 percent by weight.

21. A photoconductive imaging member in accordance with claim 20 wherein the resinous binder is a polyester, polyvinyl butyral, a polycarbonate, polyvinyl carbazole or polyvinyl formal.

22. A photoconductive imaging member in accordance with claim 3 wherein the hole transport layer comprises an aryl amine compound.

23. A photoconductive imaging member in accordance with claim 22 wherein the aryl amine comprises molecules of the formula:

dispersed in a highly insulating and transparent organic resinous binder wherein X is selected from the group consisting of alkyl and halogen.

24. A photoconductive imaging member in accordance with claim 23 wherein X is selected from the group consisting of ortho (CH₃), meta (CH₃), para (CH₃), ortho (Cl), meta (Cl), and para (Cl).

25. A photoconductive imaging member in accordance with claim 23 wherein the resinous binder is a polyester, a polyvinyl butyral, a polycarbonate, or a polyvinyl formal.

26. A photoconductive imaging member in accordance with claim 3 wherein the imaging member exhibits a dark development potential of from about $-500$ to about $-1,000$ volts.

27. A photoconductive imaging member in accordance with claim 3 wherein the imaging member exhibits a dark decay of from about $-10$ to about $-100$ volts per second.

28. A photoconductive imaging member in accordance with claim 3 wherein the imaging member exhibits a residual potential of from about 1 to about 50 volts.

29. A photoconductive imaging member in accordance with claim 3 wherein the imaging member exhibits an E ½ photosensitivity of from about 3 to about 30 ergs/cm² at 600 nanometers.

30. A method of imaging which comprises the steps of:
 (a) generating an electrostatic image on the photoconductive imaging member of claim 4;
 (b) subsequently developing the electrostatic image;
 (c) transferring the developed electrostatic image to a suitable substrate; and
 (d) permanently affixing the transferred image to the substrate.

31. A method of imaging in accordance with claim 30 wherein the electrostatic image is developed by cascade, touchdown, powder cloud, or magnetic brush methods.

32. A method of imaging in accordance with claim 30 wherein the developed electrostatic image is transferred to a substrate by means of a corotron or a biased roll.

33. A method of imaging in accordance with claim 30 wherein the substrate is paper.

34. A method of imaging in accordance with claim 30 wherein the substrate is a transparency.

35. A squaraine in accordance with claim 1 wherein alkyl contains from 1 to about 25 carbon atoms.

36. A squaraine in accordance with claim 1 wherein alkyl contains from 1 to about 12 carbon atoms.

37. A squaraine in accordance with claim 1 wherein alkoxy contains from 1 to about 25 carbon atoms.

38. A squaraine in accordance with claim 1 wherein alkoxy contains from 1 to about 12 carbon atoms.

39. A fluorinated squaraine in accordance with claim 1 wherein m is the number 1 or 2.

40. A photoconductive imaging member comprised of a photogenerating layer comprised of the squaraine of claim 1, and a hole transport layer.

41. A photoconductive imaging member comprised of a supporting substrate, a photogenerating layer comprised of a squaraine of claim 1, and a charge transport layer.

42. Squaraines selected from the group consisting of 3,4-methylenedioxyphenyl-2'-fluoro-4'-dimethylaminophenyl squaraine; 3,4-methylenedioxyphenyl-4'-dimethylaminophenyl squaraine; 3,4-methylenedioxyphenyl-2'-hydroxy-4'-dimethylaminophenyl squaraine; 3,4-methylenedioxyphenyl-2'-methyl-4'-dimethylaminophenyl squaraine; 3,4-methylenedioxyphenyl-2'-methoxy-4'-dimethylaminophenyl squaraine; 3,4-methylenedioxyphenyl-2'-chloro-4'-dimethylaminophenyl squaraine; 3,4-methylenedioxyphenyl-2',6,'-difluoro-4'-dimethylaminophenyl squaraine; 3,4-methylenedioxyphenyl-4'-N-pyrrolidinophenyl squaraine; 3,4-methylenedioxyphenyl-2'-fluoro-4'-N-pyrrolidinophenyl squaraine; 3,4-methylenedioxyphenyl-8'-fluoro-9'-julolidinyl squaraine; 3,4-methylenedioxyphenyl-2'-hydroxy-4'-N-pyrrolidinophenyl squaraine; and 3,4-methylenedioxyphenyl-2'-fluoro-4'-methylbenzyl aminophenyl squaraine.

43. A photoconductive imaging member comprised of a supporting substrate, a hole transport layer, and a photogenerating layer comprised of at least one of the squaraines of claim 42.

44. A photoconductive imaging member comprised of a hole transport layer, and a photogenerating layer comprised of at least one of the squaraines of claim 42.

45. A photoconductive imaging member comprised of a supporting substrate, a photogenerating layer comprised of a squaraine of claim 42, and a charge transport layer.

46. A photoconductive imaging member comprised of a supporting substrate, a photogenerating layer comprised of a squaraine of claim 42, and a hole transport layer.

47. A cyclized unsymmetrical squaraine represented essentially by the formula wherein $R_1$ and $R_2$ are independently selected from aliphatic and aromatic substituents; $R_3$ and $R_4$ are independently selected from aliphatic and aromatic substituents; X is hydrogen, hydroxy, alkyl, alkoxy or halogen; and m is a number of from zero to about 3.

48. A cyclized unsymmetrical squaraine represented essentially by the formula wherein $R_1$, and $R_2$ are alkyl, or hydrogen; $R_3$ and $R_4$ are alkyl, or benzyl; X is hydrogen, hydroxy, alkyl, alkoxy or halogen; and m is zero, 1, or 2.

* * * * *